United States Patent
Li et al.

(10) Patent No.: US 9,631,010 B2
(45) Date of Patent: Apr. 25, 2017

(54) AFLATOXIN NANOBODY IMMUNOABSORBENT AND IMMUNOAFFINITY COLUMN AND PREPARATION METHOD AND USE THEREOF

(71) Applicant: OILCROPS RESEARCH INSTITUTE OF CHINESE ACADEMY OF AGRICULTURE SCIENCES, Wuhan, Hubei (CN)

(72) Inventors: Peiwu Li, Hubei (CN); Qi Zhang, Hubei (CN); Yanru Wang, Hubei (CN); Zhaowei Zhang, Hubei (CN); Xiaoxia Ding, Hubei (CN)

(73) Assignee: OILCROPS RESEARCH INSTITUTE OF CHINESE ACADEMY OF AGRICULTURE SCIENCES, Wuhan, Hubei (CN)

( * ) Notice: Subject to any disclaimer, the term of this patent is extended or adjusted under 35 U.S.C. 154(b) by 0 days.

(21) Appl. No.: 15/215,056

(22) Filed: Jul. 20, 2016

(65) Prior Publication Data

US 2016/0318998 A1 Nov. 3, 2016

Related U.S. Application Data

(63) Continuation of application No. PCT/CN2014/085316, filed on Aug. 27, 2014.

(30) Foreign Application Priority Data

Mar. 28, 2014 (CN) .......................... 2014 1 0121834

(51) Int. Cl.
| | |
|---|---|
| *G01N 33/543* | (2006.01) |
| *G01N 1/40* | (2006.01) |
| *G01N 30/02* | (2006.01) |
| *C07K 1/22* | (2006.01) |
| *C07K 16/14* | (2006.01) |
| *G01N 33/569* | (2006.01) |

(52) U.S. Cl.
CPC ............... *C07K 16/14* (2013.01); *C07K 1/22* (2013.01); *G01N 33/56961* (2013.01); *C07K 2317/565* (2013.01); *C07K 2317/569* (2013.01); *G01N 2333/38* (2013.01)

(58) Field of Classification Search
CPC ........ C07K 2317/569; C07K 2317/565; C07K 2317/22; C07K 1/22; G01N 233/38; G01N 233/543; G01N 1/40; G01N 30/02; G01N 33/22
See application file for complete search history.

(56) References Cited

FOREIGN PATENT DOCUMENTS

CN 103861569 A 6/2014

OTHER PUBLICATIONS

International Search Report issued by the State Intellectual Property Office of the Peoples Republic of China dated Dec. 31, 2014 for PCT/CN2014/085316.
Yang,Chun-hong et al., "Study on factors affacting coupling reaction between polyacrylamide and the antibody of aflatoxin B1", Chinese Journal of Oil Crop Sciences, China Academic Journal Electronic Publishing House, vol. 27, No. 2, pp. 62-65, Jun. 30, 2005.
Liu, Xia et al., "Research on Panning Methods of Single-Domain Heavy-Chain Antibody Fragments for Aflatoxin B1 from Non-Immune Library", Journal of Food Science and Biotechnology, China Academic Journal Electronic Publishing House, vol. 30, No. 6, pp. 950-955, Nov. 30, 2011.
Feng, Fan et al., "Prokaryotic expression and renaturation of anti-idiotype nanobody against aflatoxin B1", Journal of Food Safety and Quality, China Academic Journal Electronic Publishing House, vol. 4, No. 4, pp. 1222-1227, Aug. 31, 2013.

*Primary Examiner* — Shafiqul Haq
*Assistant Examiner* — Carmencita M Belei
(74) *Attorney, Agent, or Firm* — Tim Tingkang Xia, Esq.; Locke Lord LLP

(57) ABSTRACT

An aflatoxin nanobody immunoabsorbent and immunoaffinity column and preparation method and use thereof. The immunoabsorbent comprises a solid phase carrier and aflatoxin B1 nanobody 2014AFB-G15 coupled with the solid phase carrier. The 50% inhibiting concentration $IC_{50}$ of aflatoxin B1 nanobody 2014AFB-G15 to aflatoxin B1 is 0.66 ng/mL, and the cross-reactivity of aflatoxin B1 nanobody 2014AFB-G15 to aflatoxins B2, G1, G2, and M1 are respectively 22.6%, 10.95%, 32.1% and 26%. The amino acid sequence of aflatoxin B1 nanobody 2014AFB-G15 is as depicted by SEQ ID NO: 7, and the coding gene sequence thereof is as depicted by SEQ ID NO: 8. The aflatoxin nanobody immunoaffinity column can be used for purification and concentration of sample extract prior to computer testing, and the immunoaffinity column can be reused repeatedly.

6 Claims, No Drawings

SEQUENCE LISTING

```
<160> NUMBER OF SEQ ID NOS: 13

<210> SEQ ID NO 1
<211> LENGTH: 8
<212> TYPE: PRT
```

<213> ORGANISM: Vicugna vicugna

<400> SEQUENCE: 1

Gly Arg Thr Phe Ser Ser Tyr Ala
1               5

<210> SEQ ID NO 2
<211> LENGTH: 7
<212> TYPE: PRT
<213> ORGANISM: Vicugna vicugna

<400> SEQUENCE: 2

Ile Ser Trp Ser Gly Gly Ser
1               5

<210> SEQ ID NO 3
<211> LENGTH: 14
<212> TYPE: PRT
<213> ORGANISM: Vicugna vicugna

<400> SEQUENCE: 3

Ala Ala Gly Phe Ser Gly Asn Tyr Tyr Arg Thr Pro Asp Tyr
1               5                   10

<210> SEQ ID NO 4
<211> LENGTH: 24
<212> TYPE: DNA
<213> ORGANISM: Vicugna vicugna

<400> SEQUENCE: 4
ggacgcacct tcagtagcta cgcc                                          24

<210> SEQ ID NO 5
<211> LENGTH: 21
<212> TYPE: DNA
<213> ORGANISM: Vicugna vicugna

<400> SEQUENCE: 5
attagctgga gtggtggtag c                                             21

<210> SEQ ID NO 6
<211> LENGTH: 42
<212> TYPE: DNA
<213> ORGANISM: Vicugna vicugna

<400> SEQUENCE: 6
gcagctggct ttagtggtaa ttactaccgc acacccgact ac                      42

<210> SEQ ID NO 7
<211> LENGTH: 130
<212> TYPE: PRT
<213> ORGANISM: Vicugna vicugna

<400> SEQUENCE: 7

Gln Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Thr Asp Ser Val
    50                  55                  60

```
Lys Gly Arg Phe Thr Ile Asn Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Gly Phe Ser Gly Asn Tyr Tyr Arg Thr Pro Asp Tyr Trp Gly
            100                 105                 110

Gln Gly Thr Gln Val Thr Val Ser Ser Glu Pro Lys Thr Pro Lys Pro
        115                 120                 125

Gln Asp
    130

<210> SEQ ID NO 8
<211> LENGTH: 390
<212> TYPE: DNA
<213> ORGANISM: Vicugna vicugna

<400> SEQUENCE: 8
cagttgcagc tcgtggagtc tgggggagga ttggtgcagg ctgggggctc tctgagactc      60
tcctgtgcag cctctggacg caccttcagt agctacgcca tgggctggtt ccgccaggct     120
ccagggaagg agcgtgagtt tgtagcggct attagctgga gtggtggtag cacatactat     180
acagactccg tgaagggccg attcaccatc aacagagaca cgccaagaa cacggtgtat      240 ctgcaaatga acagcctgaa acctgaggac acggccgttt attactgtgc agctggcttt     300
agtggtaatt actaccgcac acccgactac tggggccagg gacccaggt caccgtctcc      360 tcagaaccca agacaccaaa accacaagac                                       390

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
atgcggccca gccggcc                                                     17

<210> SEQ ID NO 10
<211> LENGTH: 46
<212> TYPE: DNA
<213> ORGANISM: Artificial Sequence
<220> FEATURE:
<223> OTHER INFORMATION: Primer

<400> SEQUENCE: 10
gatcgggccc tgtggtggtg gtggtggtgt gcggccgccc gttttc                     46

<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11
cggcgcacct gcggccgcat gggggtcttc gctgtggtgc g                          41

<210> SEQ ID NO 12
<211> LENGTH: 52
<212> TYPE: DNA
<213> ORGANISM: Artificial Sequence
<220> FEATURE:
```

```
<223> OTHER INFORMATION: Primer

<400> SEQUENCE: 12
tcctttctat gcggcccagc cggccatggc cccagktgca gctcgtggag tc          52

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
cggcgcacct gcggccgcgt cttgtggttt tggtgtcttg gg                    42
```

AFLATOXIN NANOBODY IMMUNOABSORBENT AND IMMUNOAFFINITY COLUMN AND PREPARATION METHOD AND USE THEREOF

CROSS-REFERENCE TO RELATED APPLICATIONS

This application is a continuation application of International Patent Application No. PCT/CN2014/085316, filed Aug. 27, 2014, which itself claims the priority to Chinese Patent Application No. 201410121834.8, filed Mar. 28, 2014 in the State Intellectual Property Office of P.R. China, which are hereby incorporated herein in their entireties by reference.

FIELD OF THE INVENTION

The present disclosure relates to aflatoxin nanobody immunoabsorbent and immunoaffinity column, and preparation method and use thereof.

BACKGROUND OF THE INVENTION

Aflatoxins, secondary metabolites produced by *Aspergillus flavus* and *Aspergillus parasiticus*, are natural toxic compounds that can cause various damages to human and livestock. So far, more than 20 varieties of aflatoxins have been discovered, including aflatoxin B1 ($AFB_1$), aflatoxin B2 ($AFB_2$), AFG, and M1 ($AFM_1$), and the like. Among these, $AFB_1$ has the strongest toxicity. The toxicity of $AFB_1$ is 10 times that of potassium cyanide and 68 times that of arsenic. Early in 1993, $AFB_1$ was categorized as one of the most potent carcinogenic chemicals known to International Agency for Research on Cancer of the World Health Organization, i.e., class I carcinogen. China is more severely polluted by aflatoxin, which may even exist in various food and agricultural products, especially in corn, peanut, and their products. Therefore, it is significant to reinforce detection, especially quick detection, of aflatoxin and to keep track of health information on various food and agricultural products, so that food safety in China can be guaranteed.

The existing methods for detection of aflatoxin include thin-layer chromatography, instrumental analysis and immunology analysis. Thin-layer chromatography is a common method for detection of aflatoxin at early time, which does not require special instrument and can be conducted in an average laboratory. However, thin-layer chromatography requires large dosage of reagent and complicated procedure, is seriously interfered by other components, and has poor accuracy, thus can hardly quantify precisely. In addition, thin-layer chromatography causes severe contamination hazard to experimenters and the surrounding environment, and thus is unfit for on-site detection. Instrumental analysis mainly includes fluorescence spectrophotometry and high performance liquid chromatography, which have the advantages of high sensitivity and preferable accuracy. However, the above mentioned methods require high degree of purification of aflatoxin sample. Traditional sample pre-treatment technology, such as liquid-liquid extraction, solid phase extraction and solid phase microextraction, has complicated pre-treatment procedure and less specificity. In this case, the establishment of a fast and effective sample pre-treatment has become the primary and bottleneck problem of detection and analysis of aflatoxin. Immunoaffinity column is a new type efficient sample pre-treatment technology, which implements enrichment and purification of target substance in complex samples based on reversible bonding of specificities of antigen and antibody. Immunoaffinity column combined with liquid phase chromatographic analysis, fluorescence quick-detection device and ELISA method can be widely used in the detection of aflatoxin in agricultural products and food.

At present, aflatoxin nanobody immunoaffinity column is mainly prepared by coupling of traditional antibody (polyclonal antibody or monoclonal antibody) with sepharose gel and silica gel microparticles. Since activity of the traditional antibody degenerates fast during use, it is a technical problem that the immunoaffinity column available in the market can only be repeatedly used for limited number of times. Nanobody is heavy chain antibody naturally existing in camelidae animals. So far, there is not yet any report related to aflatoxin nanobody immunoabsorbent and immunoaffinity column.

SUMMARY OF THE INVENTION

The present disclosure aims to provide aflatoxin nanobody immunoabsorbent and aflatoxin nanobody immunoaffinity column, and preparation methods and use thereof.

In order to realize the objective of the present disclosure, the following technical solution is adopted. Aflatoxin nanobody immunoabsorbent is provided, characterized in that the immunoabsorbent contains solid phase carrier and aflatoxin nanobody coupled with the solid phase carrier, wherein the aflatoxin nanobody is aflatoxin B1 nanobody 2014AFB-G15, amino acid sequence thereof as depicted in SEQ ID NO:7 and coding sequence thereof as depicted in SEQ ID NO:8.

According to the above technical solution, three complementary determining regions of the aflatoxin B1 nanobody 2014AFB-G15 respectively have amino acid sequences comprising amino acid sequence of CDR1 as depicted in SEQ ID NO:1, amino acid sequence of CDR2 as depicted in SEQ ID NO:2 and amino acid sequence of CDR3 as depicted in SEQ ID NO:3; and the three complementary determining regions thereof respectively have coding sequences comprising coding sequence of CDR1 as depicted in SEQ ID NO:4, coding sequence of CDR2 as depicted in SEQ ID NO:5 and coding sequence of CDR3 as depicted in SEQ ID NO:6.

According to the above technical solution, the solid phase carrier is sepharose gel or silica gel microparticles.

A method for preparing said aflatoxin nanobody immunoabsorbent, characterized in that, when the solid phase carrier is silica gel microparticles, the method comprises steps of: weighing 1-5 g silica gel microparticles and washing the silica gel microparticles with pure water and phosphate buffer of pH 6 alternately; suspending the silica gel microparticles in 5-25 mL of phosphate buffer of pH 6, and stirring till all silica gel microparticles are suspended, to afford silica gel microparticle suspension; dissolving 2-10 mg of aflatoxin B1 nanobody 2014AFB-G15 in 1-5 mL of phosphate buffer of pH 6, and adding resulting solution into the silica gel microparticle suspension dropwise; weighing 70-350 mg of carbodiimide and rapidly adding the carbodiimide into the silica gel microparticle suspension, and reacting under stirring at 4° C. for 18-22 h, to give aflatoxin nanobody immunoabsorbent with silica gel microparticles as the solid phase carrier; or when the solid phase carrier is sepharose gel, the method comprises the steps of: weighing 0.3-1 g of sepharose and washing the sepharose repeatedly with 1 mM of HCl solution; suspending the sepharose in 5-15 mL of coupling buffer, adding 0.6-2 mg of aflatoxin B1 nanobody 2014AFB-G15 therein, and resulting solution reacting under stirring for 1-2 h at room temperature to afford sepharose gel suspension; filtering antibody solution in the sepharose gel solution that is not coupled with the sepharose gel, and washing the sepharose gel with coupling buffer; adding 0.1 M of Tris-HCl buffer of pH 8.0, and reacting under room temperature for 2 h; and washing the sepharose gel alternately with 0.1 M of Tris-HCl buffer of pH 8.0 and 0.1 M of Tris-HCl buffer of pH 4.0, to give aflatoxin nanobody immunoabsorbent with sepharose gel as the solid phase carrier; the coupling buffer being 0.1 M $NaCO_3$ and 0.5 M NaCl of pH 8.3.

Aflatoxin nanobody immunoaffinity column loaded with aflatoxin nanobody immunoabsorbent is provided.

A method for preparing the aflatoxin nanobody immunoaffinity column is provided, comprising the steps of: filling the aflatoxin nanobody immunoabsorbent into a solid phase extraction tube, adding 0.01 M of phosphate buffer of pH 6 therein, and leaving the resulting solution to precipitate naturally; washing with 0.01 M of phosphate buffer of pH 6, and storing resulting filler in 0.01 M of phosphate buffer of pH 6 containing 0.02 wt % sodium azide, thereby obtaining aflatoxin nanobody immunoaffinity column.

A method for purification and concentration of aflatoxin B1 comprised in an extracting solution of a sample using the aflatoxin nanobody immunoaffinity column, the method comprising:

firstly rinsing the prepared aflatoxin nanobody immunoaffinity column with purified water,
then adding the extracting solution of a sample;
rinsing with purified water wherein after the liquid drain completely,
eluting with methanol, and
collecting the eluate, the eluate is purified and concentrated extraction of the sample which can be used directly for loading to a machine for detection.

The present disclosure has the following beneficial effects.

(1) A 50% inhibition concentration ($IC_{50}$) of aflatoxin B1 nanobody 2014AFB-G15 according to the present disclosure against aflatoxin B1 is 0.66 ng/ml, and cross-reactivity thereof against aflatoxin B2, G1, G2, and M1 are respectively 22.6%, 10.95%, 32.1% and 26%. A column capacity of the aflatoxin nanobody immunoaffinity column prepared according to the present disclosure is in a range of 500-600 ng, and a loading standard recovery of aflatoxin B1 thereof is in a range of 80-100 wt %.

(2) The aflatoxin nanobody immunoaffinity column according to the present disclosure has the advantages of desirable stability, thermostability, acid and alkali resistance, and resistance to organic reagent. The affinity column has long shelf life, it can be repeatedly used for multiple times, and can be used for purifying and concentrating the solution for extraction of a sample prior to detection.

(3) The aflatoxin nanobody according to the present disclosure is obtained through genetic engineering and has the advantages of low cost and easy preparation. In this case, the aflatoxin nanobody immunoaffinity column prepared with said aflatoxin nanobody is more advantageous as compared with conventional nanobody affinity column.

DETAILED DESCRIPTION OF THE EMBODIMENTS

Example 1: Establishment of Gene Library of Aflatoxin Nanobody and Preparation of the Nanobody 1. Animal Immunization was Performed.

A two year-old male alpaca and antigen for immunization to aflatoxin B1 (AFB1-BSA, manufactured by Sigma company) were purchased. 200 μg of aflatoxin B1 antigen was emulsified with Freund's incomplete adjuvant, and the alpaca was injected with resulting emulsion subcutaneously at several sites. The alpaca was immunized every three weeks, and vein blood was sampled on the $7^{th}$ to $10^{th}$ day after each immunization. A titer of the serum was measured by an indirect ELISA method. An immunization with the highest titer was selected, and 10 ml blood was sampled, from which total RNA was extracted.

2. A cDNA Library was Established.

(1) Total RNA was extracted. An immunization with the highest titer was selected. 10 mL blood was sampled from the alpaca on the $7^{th}$ to $10^{th}$ day after the immunization, from which the total RNA was extracted. The total RNA in the blood sample of the alpaca was extracted with a Leuko-LOCK total RNA isolation system manufactured by Life Technology Company.

(2) Synthesis of cDNA was conducted. Reverse transcription was performed following a reverse transcriptase instruction of the Promega company, with the total RNA obtained from the above part (1) as a template, and oligo $(dT)_{15}$ as a primer, to synthesize a first strand cDNA and obtain a cDNA library.

3. An Aflatoxin Nanobody Gene Library was Established.

(1) PCR amplification was performed to obtain heavy chain antibodies variable-domain genes of the alpaca, i.e., VHH genes, with cDNA synthesized according to the above section 2 as a template, and with R1 and F, or R2 and F, as primer. 2 μl of cDNA, 5 μl of 10×PCR buffer, 2 μl of 50 mM $MgSO_4$, 1 μl of 10 mmol/L dNTP, 1 μl of 10 μmol/L primer F, 1 μl of 10 μmol/L primer R1 (or R2), 0.1 μl of DNA polymerase, and 37.9 μl of sterile pure water were vortex mixed uniformly, to afford 50 μl of mixed solution. After brief centrifugation of the resulting mixed solution, PCR amplification reaction was performed under reaction conditions including denaturation at 94° C. for 2 min, and subsequent denaturation at 94° C. for 30 s, annealing at 55° C. for 30 s, extension at 68° C. for 1 min, and 30 circulations, and then extension at 68° C. for 5 min.

R1 was 5-CGGCGCACCTGCGGCCGC ATGGGGGTCTTCGCTGTGGTGCG-3' (SEQ ID NO:11), R2 was 5'-CGGCGCACCTGCGGCCGC GTCTTGTG-GTTTTGGTGTCTTGGG-3' (SEQ ID NO:13), and F was 5'-TCCTTTCTATGCGGCCCAGCCGGCCATGGCCC CAGKTGCAGCTCGTGGAGTC-3' (SEQ ID NO:12), in which the underlined parts of the primer sequences were homologous with pCANTAB 5E (his) vector. 4 times of PCR amplification reaction, with R1 and F as the primer, and 6 times of PCR amplification reaction, with R2 and F as the primer, were performed. Resulting PCR product was separated by 0.7% agarose gel electrophoresis, and DNA fragments of 450 bp were purified and recovered with a kit.

(2) pCANTAB 5E (his) vector was constructed. PCR amplification of DNA fragments from Sfi I to Not I on pCANTAB5E vector plasmid was performed, with pCANTAB5E vector plasmid as a template, p5E SfiI-F: 5'-ATGCGGCCCAGCCGGCC-3' (Sfi I, (SEQ ID NO:9) as upstream primer and p5E N-P-H-R: 5'-GATCGGGCCCT-GTGGTGGTGGTGGTGGTGTGCGGCCGCCCGTTTTC-3' (SEQ ID NO:10) as downstream primer, to give p5E-his fragment. Subsequently, the p5E-his fragment was digested by Sfi I enzyme, followed by PspoMI enzyme, to give p5E-his (Sfi I/PspoMI) with cohesive end; and the pCANTAB5E vector plasmid was digested by Sfi I enzyme, followed by Not I enzyme, to give p5E (Sfi I/Not I) with cohesive end. The p5E-his (Sfi I/PspoMI) with cohesive end and the p5E (Sfi I/Not I) with cohesive end were ligated, to afford pCANTAB 5E (his) vector.

(3) The pCANTAB 5E (his) was treated by double enzyme digestion. Sfi I enzyme digestion was performed. Reaction solution was prepared according to the following system: 30 μl of pCANTAB 5E (his) vector, 1 μl of Sfi I, 10 μl of 10×M buffer, and the total solution was filled with ddH$_2$O till a volume thereof reached 100 μl. The reaction solution was incubated in water bath at 50° C. for 2 h, and the resulting product was recovered by agarose gel DNA purification kit.

Not I digestion was performed. Reaction solution was prepared according to the following system: 30 μl of product recovered from Sfi I single enzyme digestion of pCANTAB 5 E (his), 1 μl of Not I, 10 μl of 10×H buffer, and the total solution was filled with ddH$_2$O till a volume thereof reached 100 μl. The reaction solution was incubated in water bath at 37° C. for 4 h, and resulting product was recovered by agarose gel DNA purification kit.

(4) VHH gene was ligated with pCANTAB 5 E (his) vector treated by double enzyme digestion. An In-Fusion ligation was performed according to the following system: 120 ng of pCANTAB 5 E (his) vector treated by Sfi I/Not I double enzyme digestion, 40 ng of VHH genes, 2 μl of 5×In-Fusion buffer, 1 μl of In-Fusion enzyme, and the total solution was filled with ddH$_2$O till a volume thereof reached 10 μl. The reaction solution was incubated in water bath at 37° C. for 15 min, and then in water bath at 50° C. for 15 min. The resulting solution was placed on ice immediately after the water baths and kept for 5 min. Into the resulting solution was added 40 μl of TE buffer. The resulting product was recovered by agarose gel DNA purification kit and kept at −20° C. for later use.

(5) Electroportation of ligation product was performed. Into 50 μl of E. coli TG1 electroporation-competent cells was added 5 μl of said ligation product. The resulting mixture was mixed uniformly and added into a pre-cooled 0.1 cm-gap electroporation cuvette (manufactured by Bio-RAD). The electroporation cuvette was kept on ice for 10 min, and subsequently put on an electroporator for electroporation. Electroporation conditions included 1.8 kV, 200Ω, and 25 μF. 1 ml of 2YT fluid medium was added into the electroporation cuvette immediately after the electroporation. After pipetting up and down, the resulting mixture was transferred into a sterilized and clean 15 mL shaking tube. The mixture was slowly shaken at 37° C. for 1 h for revival of the bacteria. 2 μl of the bacterial culture was serially diluted and plated on LB plates with ampicillin. The plates were placed upside down at 37° C. overnight. The next day, library capacity was calculated by counting the number of bacterial colonies.

(6) Rescue of the aflatoxin nanobody gene library is performed. 10 times of the above-mentioned electroporation were performed. The revived bacterial culture was completely transferred into 200 mL of SB medium and shaken at 250 rpm at 37° C. till an OD$_{600}$ thereof was 0.5. 1 mL of 1×10$^{12}$ pfu helper phage M13KO7 was added into the bacterial suspension culture. After the resulting culture was kept standing at 37° C. for 1 h, it was further shaken for 2 h. Kanamycin was added into the resulting culture till a final concentration of kanamycin was 70 μg/mL. The resulting culture was shaken overnight. On the next day, the resulting bacterial suspension culture was centrifuged at 10,000 rmp for 15 min at 4° C. The resulting supernatant was transferred into a sterile centrifuge bottle, and was added with ¼ volume of 5×PEG/NaCl, kept standing on ice for 2 h, and then centrifuged at 12,000 rmp for 20 min 4° C. The resulting precipitate was dissolved in 10 mL of sterile resuspension solution (PBS buffer containing 1×proteinase inhibitor, 0.02% NaN$_3$ and 0.5% BSA) to obtain the aflatoxin nanobody gene library rescued by the phage.

4. Panning of Aflatoxin B1 Nanobody.

ELISA plates were respectively coated with AFB$_1$-BSA (1 μg/well) and 3% BSA-PBS solution (used as a negative control) and kept at 4° C. overnight. The next day, the coating buffer was discarded. The plates were washed with PBST for 3 times, and blocked with 3% skimmed milk powder for 1 h. The plates were washed with PBST for 3 times, and 50 μl of the above rescued aflatoxin nanobody gene library was added into each well coated with AFB$_1$-BSA, and then incubated at 37° C. for 1 h. The plate was washed with PBST for 10 times, and 100 μl of 100 ng/mL AFB$_1$ solution was added into each well. The plate was eluted by shaking at room temperature (20° C.-30° C.) for 30 min. The eluate was transferred to the wells coated with 3% BSA-PBS solution. The plate was incubated at 37° C. for 1 h (to remove non-specific adsorption). After incubation, the supernatant was taken to infect 2 mL of TG1 bacterial culture which has grown to a logarithmic phase, and the infection was sustained at 37° C. for 20 min. 1 μl and 10 μl of the infected bacterial culture were respectively taken and plated onto LB-ampicillin plates. The LB-ampicillin plates were kept standing in an incubator at 37° C. overnight. The next day, the phage titer in the eluate was determined by counting the number of the colonies on the plates. The remaining infected TG1 bacterial culture was transferred into 6 mL of SB medium, into which was added 1.5 μl of 100 mg/mL ampicillin, shaken at 37° C. for 1 h, and supplemented with ampicillin to reach a final concentration of 50 μg/mL; further shaken for 1 h, added with 1 mL of helper phage M13KO7 (1×10$^{12}$ pfu/mL), and kept standing at 37° C. for 30 min. The bacterial culture was then transferred into 100 mL of SB medium, added with 46 μl of ampicillin (100 mg/mL), further shaken for 2 h, supplemented with kanamycin to reach a final concentration of 70 μg/mL, and shaken at 37° C. overnight. The next day, the bacterial culture was centrifuged at a speed of 10,000 rpm for 15 min at 4° C. Supernatant was transferred therefrom, and then added with ¼ volume of PEG/NaCl solution, incubated on ice for 2 h, and centrifuged at a speed of 12,000 rpm for 20 min at 4° C. Pellet was dissolved in 1% BSA-PBS solution to obtain amplified product of the first round of panning. The amplified product was kept for use in the next round. In subsequent rounds of panning, concentrations of coating antigen AFB$_1$-BSA were respectively 0.5 μg/well, 0.1 μg/well, and 0.05 μg/well, and eluates were respectively AFB$_1$ solutions of 500 ng/mL, 100 ng/mL, and 50 ng/mL.

5. Identification of Positive Clones

After 4 rounds of panning, 2 μl of eluate was serially diluted, and taken to infect TG1 bacterial culture which has grown to the logarithmic phase. The infected TG1 bacterial culture was plated onto LB-ampicillin plates. The plates were placed upside down and incubated at 37° C. overnight. The next day, 30 clones were randomly picked, and each were added into 3 mL of SB-ampicillin culture medium, and then were shaken to be cultured at 37° C. for 6-8 h until the $OD_{600}$ was about 0.6. The bacterial culture was added with 30 µl of helper phage M13KO7 ($1\times10^{12}$ pfu/mL), kept standing at 37° C. for 30 min, and then further shaken for 2 h. The bacterial culture was supplemented with kanamycin to reach a final concentration of 70 µg/mL, and then shaken to be cultured overnight. The next day, the bacterial culture was centrifuged at a speed of 10,000 rpm for 15 min at 4° C. to obtain the supernatant of the bacterial culture.

$AFB_1$-BSA solution was prepared in coating solution until a final concentration reached 0.2 µg/mL. The prepared $AFB_1$-BSA solution was taken to coat a 96-well ELISA plate, with 100 µl in each well. In the meantime, another ELISA plate was taken, with 32 wells thereof each being coated with 3% BSA, at 4° C. overnight. The next day, the solution was discarded, and the plate was washed with PBST for 3 times and blocked with 3% skimmed milk powder-PBS for 1 h. $AFB_1$ standard stock solution was taken to prepare working solutions respectively having concentrations of 100 ng/mL and 0 ng/mL with 10% methanol/PBS. The working solutions were respectively added into wells coated with $AFB_1$-BSA antigen. Into each well was added 50 µl of the above-mentioned supernatant of the bacterial culture. The assay with working solution of each concentration was repeated for 3 times. 10% methanol/PBS and 50 µl of the above-mentioned supernatant of the bacterial culture were added into each well coated with BSA as control and mixed uniformly by gently shaking the plate. The plate was placed at a 37° C. incubator to react for 1 h. The plate was washed with PBST for 10 times. Subsequently, into each well was added 100 µl of HRP/ANTI-M13, which had been diluted with PBS in a proportion of 1:5000, and the plate was incubated at 37° C. for 1 h. Followed was 6 washes with PBST. Into each well was added 100 µl freshly prepared TMB substrate solution, and the plate was incubated at 37° C. for 15 min. 50 µl of 2 mol/L $H_2SO_4$ was added into each well to terminate the reaction; and $OD_{450}$ values were respectively measured by a microplate reader. The positive phage clones were those that did not adsorb BSA, but adsorbed $AFB_1$-BSA and competed with the aflatoxin added. The wells having both relatively high absorbance and sensitivity were selected, thereby obtaining phage-displayed aflatoxin B1 nanobody 2014AFB-G15.

Antibody specificity of aflatoxin B1 nanobody 2014AFB-G15 measured by indirect competitive ELISA method can be specifically described in terms of cross reactivity. The method is as follows. Five different standard stock solutions of $AFB_1$, $AFB_2$, $AFG_1$, $AFG_2$, and $AFM_1$ were respectively diluted with 10% methanol/PBS in gradient to ten different working concentrations, so as to determine the antibody specificity by indirect competitive ELISA method under the same conditions. Competitive ELISA curves of the five aflatoxins were drawn successively and respective concentrations of standard substance of an inhibition ratio of 50% represented by $IC_{50}$ were calculated. Cross reactivities were calculated based on the following formula: cross reactivity (%)=($AFB_1 IC_{50}$/analogue $IC_{50}$)×100%. In the formula, the analogue can be $AFB_2$, $AFG_1$, $AFG_2$ or $AFM_1$. 50% inhibiting concentration of aflatoxin B1 nanobody 2014AFB-G15 against aflatoxin B1 obtained was 0.66 ng/mL, and cross reactivities thereof to aflatoxins B2, G1, G2 and M1 were respectively 22.6%, 10.95%, 32.1% and 26%. In this case, aflatoxin B1 nanobody 2014AFB-G15 was a specific antibody against aflatoxin B1. Tolerance experiments showed that resistance to organic solvents of aflatoxin B1 nanobody 2014AFB-G15 was improved by 35% and resistance to high temperature thereof was improved by 46%, as compared with conventional murine source antibodies and rabbit source antibodies.

The selected cloned bacterial culture containing aflatoxin B1 nanobody 2014AFB-G15 was sent to Shanghai Sunny Biotechnology Co., Ltd. for sequencing analysis, with universal primer R1 for phage vector 5'-CCA TGA TTA CGC CAA GCT TTG GAG CC-3'. Amino acid sequence of the obtained aflatoxin B1 nanobody 2014AFB-G15 is as depicted in SEQ ID No:7 and a coding sequence thereof is as depicted in SEQ ID No:8. Three complementary determining regions of the aflatoxin B1 nanobody 2014AFB-G15 respectively had amino acid sequences comprising amino acid sequence of CDR1 as depicted in SEQ ID NO:1, amino acid sequence of CDR2 as depicted in SEQ ID NO:2 and amino acid sequence of CDR3 as depicted in SEQ ID NO:3; and the three complementary determining regions thereof respectively had coding sequences comprising coding sequence of CDR1 as depicted in SEQ ID NO:4, coding sequence of CDR2 as depicted in SEQ ID NO:5 and coding sequence of CDR3 as depicted in SEQ ID NO:6.

6. Preparation and Purification of Aflatoxin Nanobody 2014AFB-G15.

(1) TG1 bacterial culture capable of secreting aflatoxin B1 nanobody 2014AFB-G15 was obtained. Plasmids were extracted with a DNA mini-extraction kit of Qiagen and transformed into HB2151 competent cells. The transformed competent cells were plated onto LB-ampicillin plates.

(2) HB2151 colonies containing aflatoxin B1 nanobody 2014AFB-G15 plasmids were selected and inoculated into a 100 mL SB-ampicillin liquid medium, and cultured at a speed of 250 rpm at 37° C. until $OD_{600}$ was in a range of 0.5-0.8. 200 µl of 0.5 M IPTG solution was added into the culture for induction overnight.

(3) The resulting culture after induction was centrifuged at a speed of 10,000 rpm for 15 min at 4° C. The supernatant was carefully removed in a sterile operation bench, and soluble protein was extracted from bacterial cell pellets by an osmotic shock method, so as to obtain supernatant containing the protein. The supernatant containing the protein was filtered through a 0.22 µm filter membrane, and dialyzed in equilibration buffer (containing 50 mM phosphate, 300 mM sodium chloride, and 20 mM imidazole; pH 7.4) overnight.

(4) The antibodies were purified by a His60 nickel column (manufactured by Clontech Technology). Firstly, the nickel column was rinsed with 10 column volumes of equilibration buffer. The supernatant containing the protein dialyzed in the above step (3) was loaded to the His60 nickel column (Clontech Technology) for antibody purification. Subsequently, the column was washed with 10 column volumes of rinsing buffer (containing 50 mM phosphate, 300 mM sodium chloride, and 40 mM imidazole; pH 7.4). At last, antibody 2014AFB-G15 was eluted with 10 column volumes of elution buffer (containing 50 mM phosphate, 300 mM sodium chloride, and 300 mM imidazole; pH 7.4). Resulting eluate was collected and put into a dialysis bag, dialyzed with 0.01 M phosphate buffer of pH 7.4 for 2 to 3 days, and then concentrated. The concentrated eluate was fractionized and stored at −20° C. for later use.

Example 2: Preparation of Aflatoxin Nanobody Immunoabsorbent and Immunoaffinity Column The immunoabsorbent according to the present example contained solid phase carrier (silica gel microparticles) and aflatoxin B1 nanobody 2014AFB-G15 coupled with the solid phase carrier. The immunoabsorbent was specifically prepared according to the following method. 1 g of acrylamide silica gel microparticles were weighed and put into a conical flask, and washed alternately with pure water and phosphate buffer of pH 6. 5 mL of phosphate buffer of pH 6 was measured to suspend the microparticles, and microparticle suspension was obtained. The microparticle suspension was transferred into a stirring cup and agitated with a stirrer until all the microparticles suspended. 2 mg of aflatoxin B1 nanobody 2014AFB-G15 was dissolved in 1 mL of phosphate buffer of pH 6, and added into the above obtained microparticle suspension dropwise. 70 mg of EDC was weighed and rapidly added into to the stirring cup, and stirred at 4° C. for 18-22 h, to give aflatoxin nanobody immunoabsorbent.

The aflatoxin nanobody immunoaffinity column was prepared according to the following method. 0.2 mL of the above obtained immunoabsorbent was filled into a solid phase extraction tube. 0.01 M of phosphate buffer of pH 6 was added into the solid phase extraction tube for natural precipitation. Resulting precipitate was washed with 0.01 M of phosphate buffer of pH 6, and then kept in 0.01 M of phosphate buffer of pH 6 containing 0.02 wt % of sodium azide, to give aflatoxin nanobody immunoaffinity column. The aflatoxin nanobody immunoaffinity column was kept at 4° C. as standby.

Example 3: Preparation of Aflatoxin Nanobody Immunoabsorbent and Immunoaffinity Column The immunoabsorbent according to the present example contained solid phase carrier (sepharose) and aflatoxin B1 nanobody 2014AFB-G15 coupled with the solid phase carrier. The immunoabsorbent was specifically prepared according to the following method. 0.3 g of sepharose was taken and put into a conical flask, and repeatedly washed with 1 mM of HCl solution for over 15 min. The sepharose was suspended in 5 mL of coupling buffer (0.1 M of $NaCO_3$ and 0.5 M of NaCl; pH 8.3). 0.6 mg of aflatoxin B1 nanobody 2014AFB-G15 was added into the mixture containing sepharose and stirred at a speed of 150 rmp at room temperature for 1 h, to afford sepharose gel suspension. The sepharose gel suspension was transferred into a sand-core funnels, so that solution containing antibody that hadn't coupled can flow out. The sepharose gel was washed with coupling buffer of 5 times the volume of the sepharose gel. Then, block buffer (0.1 M Tris-HCl of pH 8.0) of 2 times the volume of the sepharose gel was added for reaction at room temperature for 2 h. Subsequently, the sepharose gel was washed alternately with buffer of high pH (0.1 M Tris-HCl of pH 8.0) and buffer of low pH (0.1 M Tris-HCl of pH 4.0) for three times, and aflatoxin nanobody immunoabsorbent was obtained.

The aflatoxin nanobody immunoaffinity column was prepared according to the following method. 0.2 mL of the above obtained immunoabsorbent was filled into a solid phase extraction tube. 0.01 M of phosphate buffer of pH 6 was added into the solid phase extraction tube for natural precipitation. Resulting precipitate was washed with 0.01 M of phosphate buffer of pH 6, and then kept in 0.01 M of phosphate buffer of pH 6 containing 0.02 wt % of sodium azide, to give aflatoxin nanobody immunoaffinity column. The aflatoxin nanobody immunoaffinity column was kept at 4° C. as standby.

Example 4: Measurement of Column Capacity of the Aflatoxin Nanobody Immunoaffinity Column The immunoaffinity column prepared according to example 2 or example 3 was washed with 10 mL pure water. Aflatoxin B1 standard solution (having a concentration of 100 ng/mL, and a total content of aflatoxin B1 of 1 mg) dissolved in 10 mL 10% methanol/PBS was passed through the column. The column was washed with 10 mL of pure water, so that unbound aflatoxin can be removed. Finally, the column was eluted with 5 mL of methanol solution. Resulting eluate was collected and fractionized with tubes, with 1 mL in each tube. The content of aflatoxin in the eluate was measured by liquid chromatography method. Results indicated that a column capacity of the aflatoxin nanobody immunoaffinity column is in a range of 500-600 ng. After the immunoaffinity column was used repeatedly for five times, the column capacity thereof can still reach 480 ng. In this case, the immunoaffinity column can be repeatedly used. In the meantime, as shown by results of the cross reactivity measurement, the aflatoxin nanobody immunoaffinity column according to the present disclosure can specifically bind to aflatoxin B1, B2, G1, G2 and M1 simultaneously, but would not bind to other fungaltoxin, such as zearalenone, vomitoxin, ochratoxin, and the like.

Example 5: Measurement of Loading Standard Recovery of the Aflatoxin Nanobody Immunoaffinity Column For each of peanuts, corn, vegetable oil and fodder, three blank samples that contain no aflatoxin were prepared, each weighed 5 g. Into every three blank samples were respectively added 50 ng, 250 ng and 500 ng of aflatoxin B1 standard substance. Conventional ultrasonic extraction was performed at 50° C. for 10 min using 15 mL of 70% methanol-water (containing 4% NaCl). The extraction solution was filtered through filter paper. 2 mL of petroleum ether was added into 4 mL of filtrate. The mixture was vortexed uniformly and stood for stratification. 3 mL was taken from a bottom layer and added with 8 mL of pure water, and resulting mixture was filtered through a 0.45 μm organic membrane to afford filtrate, i.e., sample extraction solution. The immunoaffinity column prepared according to example 2 or example 3 was washed with 10 mL of pure water, loaded with 8 mL of said sample extraction solution, and then eluted with 10 mL of pure water. After fluid was drained, the immunoaffinity column was eluted with 1 mL of methanol. Eluate was collected and loaded on a high performance liquid chromatography, so that the content of aflatoxin in the eluate can be detected. Subsequently, the recovery was calculated. Result indicated that an average recovery rate of aflatoxin B1 of the aflatoxin nanobody immunoaffinity column is in a range of 80-100 wt %.

What is claimed is:

1. An aflatoxin B1 nanobody immunosorbent, comprising:
 a solid phase carrier; and
 an aflatoxin nanobody coupled to the solid phase carrier, wherein the aflatoxin nanobody consists of aflatoxin B1 nanobody 2014AFB-G15, wherein the aflatoxin B1 nanobody 2014AFB-G15 comprises
the amino acid sequence of SEQ ID NO:7, encoded by the nucleic acid sequence of SEQ ID NO:8; wherein the aflatoxin B1 nanobody 2014AFB-G15 comprises further three complementary determining regions of: CDR1 consisting of amino acid sequence of SEQ ID NO: 1; CDR2 consisting of amino acid sequence of SEQ ID NO:2; and CDR3 consisting of amino acid sequence of SEQ ID NO:3; wherein the CDR1 is encoded by the nucleic acid sequence of SEQ ID NO:4; the CDR2 is encoded by the nucleic acid sequence of SEQ ID NO:5; and the CDR3 is encoded by the nucleic acid sequence of SEQ ID NO:6; and wherein the aflatoxin B1 nanobody immunosorbent specifically binds aflatoxin B1.

2. The aflatoxin B1 nanobody immunoabsorbent according to claim 1, wherein the solid phase carrier is sepharose gel or silica gel microparticles.

3. A method for preparing the aflatoxin nanobody immunoabsorbent according to claim 1, wherein the solid phase carrier is silica gel microspheres or sepharose gel, wherein when the solid phase carrier is silica gel microparticles, the method comprises; weighing 1-5 g silica gel microparticles and alternatively washing the silica gel microparticles with pure water and phosphate buffer of pH 6; suspending the silica gel microparticles in 5-25 ml phosphate buffer of pH 6, and stirring to obtain a silica gel microparticle suspension; dissolving 2-10 mg of the aflatoxin B1 nanobody 2014AFB-G15 in 1-5 mL of phosphate buffer of pH 6; adding dropwise the dissolved aflatoxin B1 nanobody 2014AFB-G15 solution to the silica gel microparticle suspension; weighing 70-350 mg of carbodiimide and rapidly adding the carbodiimide into the silica gel microparticle suspension having the aflatoxin B1 nanobody 2014AFB-G15; and reacting under stirring at 4° C. for 18-22 h, to obtain the aflatoxin nanobody immunoabsorbent with silica gel microparticles as the solid phase carrier; or when sepharose gel is the solid phase carrier, the method comprises: weighing 0.3-1 g sepharose gel; washing the sepharose gel repeatedly with 1 mM of HCl solution; suspending the washed sepharose in 5-15 mL of coupling buffer, adding 0.6-2 mg of aflatoxin B1 nanobody 2014AFB-G15 to the sepharose gel in coupling buffer and reacting under stirring for 1-2 h at room temperature to obtain a sepharose gel suspension wherein aflatoxin B1 nanobody 2014AFB-G15 is coupled to the sepharose gel; filtering the unreacted aflatoxin B1 nanobody solution from the sepharose gel and washing the filtered sepharose gel with coupling buffer; adding 0.1 M of Tris-HCl buffer of pH 8.0 to the washed sepharose gel; and reacting under room temperature for 2 h; and alternatively washing the washed sepharose with 0.1 M of Tris-HCl buffer of pH 8.0 and 0.1 M of Tris-HCl buffer of pH 4.0, to obtain the aflatoxin nanobody immunoabsorbent with sepharose gel as the solid phase carrier,
 wherein the coupling buffer is 0.1 M $NaCO_3$ and 0.5 M NaCl having pH 8.3.

4. An aflatoxin B1 nanobody immunoaffinity column loaded with the aflatoxin B1 nanobody immunoabsorbent according to claim 1.

5. A method for preparing the aflatoxin B1 nanobody immunoaffinity column of claim 4, comprising: filling the aflatoxin B1 nanobody immunoabsorbent into a solid phase extraction tube; adding 0.01 M of phosphate buffer of pH 6 therein and allowing the resulting solution to precipitate naturally; washing with 0.01 M of phosphate buffer of pH 6; and storing in 0.01 M of phosphate buffer of pH 6 containing 0.02 wt % sodium azide, thereby obtaining aflatoxin B1 nanobody immunoaffinity column.

6. A method for purification and concentration of aflatoxin B1 comprised in an extracting solution of a sample using the aflatoxin nanobody immunoaffinity column of claim 4, the method comprising:
 firstly rinsing the prepared aflatoxin B1 nanobody immunoaffinity column with purified water; then adding the extracting solution of a sample to the rinsed aflatoxin nanobody immunoaffinity column; rinsing with purified water to remove unbound aflatoxin nanobody from the column; after the liquid drains completely, eluting with methanol; and collecting the eluate,
 wherein the eluate comprises purified and concentrated aflatoxin which can be used directly for loading to a machine for detection.

* * * * *